United States Patent [19]
van Gijzel

[11] Patent Number: 4,971,437
[45] Date of Patent: Nov. 20, 1990

[54] OPTICAL SPECTRAL ANALYSIS SYSTEM AND METHOD

[75] Inventor: Pieter van Gijzel, Houston, Tex.

[73] Assignee: Texaco Inc., White Plains, N.Y.

[21] Appl. No.: 890,208

[22] Filed: Jul. 28, 1986

[51] Int. Cl.⁵ .................... G01N 21/59; G01N 21/64
[52] U.S. Cl. .................................. 356/73; 250/461.1; 356/417; 356/418; 356/419
[58] Field of Search ................ 356/417, 418, 419, 73, 356/414; 250/458.1, 459.1, 461.1, 461.2

[56] References Cited

U.S. PATENT DOCUMENTS

| | | | |
|---|---|---|---|
| 3,437,411 | 4/1969 | Rudomanski et al. | 356/418 |
| 3,748,044 | 7/1973 | Liston | 356/414 |
| 3,787,695 | 1/1974 | West | 356/417 |
| 3,920,334 | 11/1975 | Steichen et al. | 250/461.1 |
| 4,030,829 | 6/1977 | Hooper | 356/325 |

OTHER PUBLICATIONS

Khalil et al., *Clinical Chemistry*, vol. 27, No. 9, 1981, pp. 1586–1591.
Alpert, *Clinical Instrument Systems*, vol. 2, No. 8, Aug. 1981, pp. 1–5.

Primary Examiner—F. L. Evans
Attorney, Agent, or Firm—Robert A. Kulason; James J. O'Loughlin; Ronald G. Gillespie

[57] ABSTRACT

The present invention is an optical spectral analysis system and method which includes transmitting light through a specimen to be analyzed. The light that is passed through the specimen is filtered. The filtering of the light is obtained by utilizing a revolving filter disk which filters the light from the specimen through a predetermined range of light wavelengths at least once per revolution. The disk is rotated by a motor. A photomultiplier tube, with associated circuitry, receives the filtered light and provides a signal representative of the intensity of the received filtered light. A computer converts the signal from the photomultiplier circuit to a spectral output.

8 Claims, 3 Drawing Sheets

OPTICAL SPECTRAL ANALYSIS SYSTEM AND METHOD

BACKGROUND OF THE INVENTION

Field of the Invention

The present invention relates to spectral analysis systems and methods in general and, more particularly, to an optical spectral analysis system and method.

SUMMARY OF THE INVENTION

The present invention is an optical spectral analysis system and method which includes transmitting light through a specimen to be analyzed. The light that is passed through the specimen is filtered. The filtering of the light is obtained by utilizing a revolving filter disk which filters the light from the specimen through a predetermined range of light wavelengths at least once per revolution. The disk is rotated by a motor. A photomultiplier tube, with associated circuitry, receives the filtered light and provides a signal representative of the intensity of the received filtered light. A computer converts the signal from the photomultiplier circuit to a spectral output.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE INVENTION

Heretofore microscope-photometer systems for spectral fluorescence analysis encountered several problems when the fluorescence of small or faintly fluorescent geologic materials was analyzed. The problems encountered by the prior art microscope-photometer systems were that light emitted by geologic particles usually has so little intensity that a high amplification of the photomultiplier signals is needed which results in a strong electronic noise that overlays the spectral curve and makes the curve inaccurate. Further, a mercury vapor lamp is used as the UV-light source for fluorescence microscopes. Fluctuations in the radiation of this lamp type often occur and have a similar effect on the spectral curve as the electronic noise. The frequency of these fluctuations usually is in some seconds or more.

Another problem was that geologic materials, like biologic tissues, show a change in fluorescence color and spectrum within a few seconds after irradiation begins. These changes are a result of photochemical reactions of the materials. The real fluorescence spectrum can only be obtained with extremely short times of spectral scanning. The time needed by the prior art systems is much too long, 15 seconds at best, and the principles on which these systems are based do not allow a large reduction of the measuring time. Repeated scanning and averaging of spectra is also needed due to the small fluorescence intensities. This results in a greater effect of the photochemical reactions (often described as fading) on the measured spectrum.

For decades spectrofluorimeters were used in the analysis of chemical compounds and solutions. These equipments have a better spectral resolution and are less prone to electronic noise than the microscope photometers. However, such equipment is too heavy and unsuitable to be mounted on a microscope.

Figure 1:
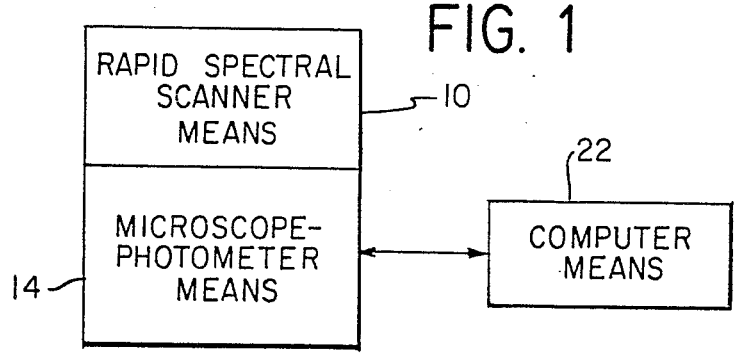
FIG. 1 is a simplified block diagram of an optical spectral analysis system constructed in accordance with the present invention.

The present invention solves these problems. With reference to FIG. 1, there is shown rapid spectral scanning means 10, microscope-photometer means 14, and computer means 22. Microscope-photometer means 14 is purchased equipment which may either be provided by Leitz or Zeiss. Both are well known manufacturers of optical equipment. Computer means 22 may be a general purpose digital computer electrically connected to the microscope photometer means 14 which provides electrical signals corresponding to the light passing through the subject on this particular invention. A signal relating to the positioning of a filter will be described in a discussion of the rapid spectral scanning means 10.

Figure 2:
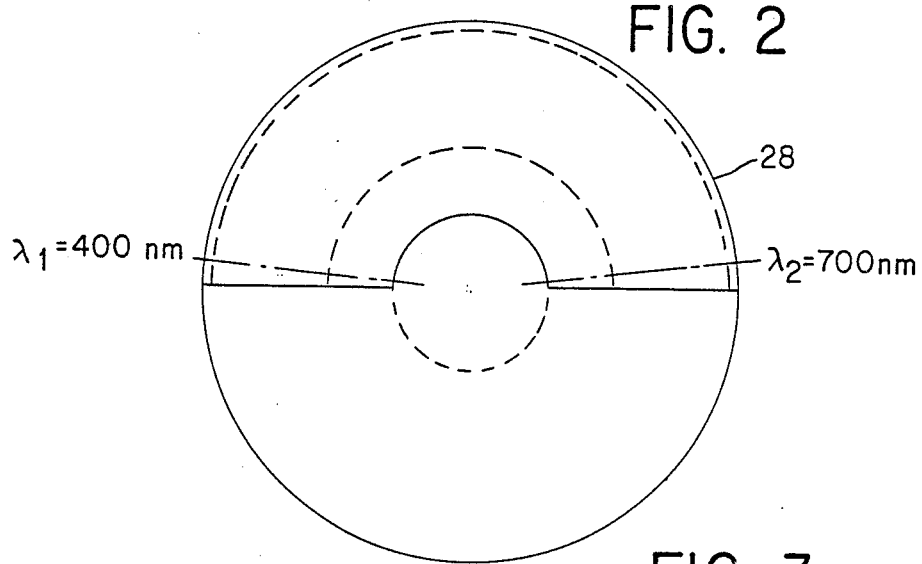
FIG. 2 is a filter disk which is part of the rapid spectral scanning means shown in FIG. 1.
Figure 3:
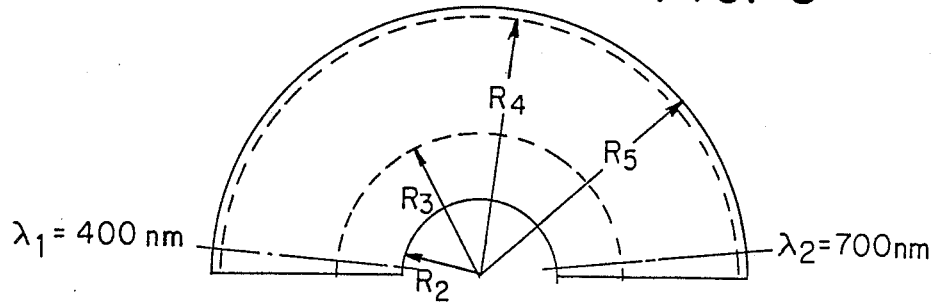
FIG. 3 is a light filter which is used in the filter disk shown in FIG. 2.

Rapid spectral scanning means 10 includes a disk filter 28 shown in FIG. 2. Disk filter 28 is made up of two identical half filter shown in FIG. 3. The half filter shown in FIG. 3 is an item manufactured by Optical Coating Laboratory, Inc. It will pass a minimum wavelength $\lambda 1$ equal to 400 nm to a maximum wavelength $\lambda 2$ equal to 700 nm in a continuous gradation of filtrate material. $R_1$, $R_2$, $R_3$ and $R_3$ relate to the radii of the half disk. $R_1$ is two inches, as can be seen and relates to the outer radius of filter 28. Radius $R_2$ is the inner radius of filter 28 and is a half-inch. Radii $R_3$ and $R_4$ define a light pathway as in FIG. 5 which would pass through filter 28 as hereinafter described.

Figure 4:
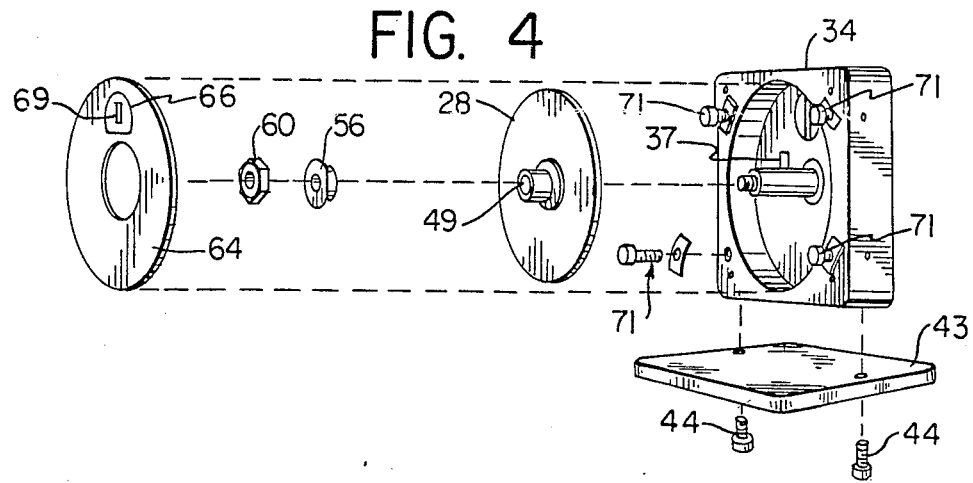
FIG. 4 is a simplified assembly type drawing showing the housing for the filter disk of FIG. 2 which is used in the rapid spectral scanning means of FIG. 1.

With reference to FIG. 4 there is shown in more detail the utilization of filter disk 28. Filter disk 28 is located in an assembly including a housing 34 having a shaft 37. Housing 34 is mounted to a base plate 43 with mounting screws 44. Filter 28 is placed onto shaft 37 by use of a filter hub 49. A thrust bearing 56 is also utilized with the mounting of filter 28 which is locked in place with a clamping nut 60. A cover plate 64 is mounted next and includes a removable slit plate 66. Cover plate 64 is held in place to the housing by clamps 71.

When fully assembled, filter 28 is rotated by a synchronous motor (not shown) at 60 revolutions per second.

Figure 5:
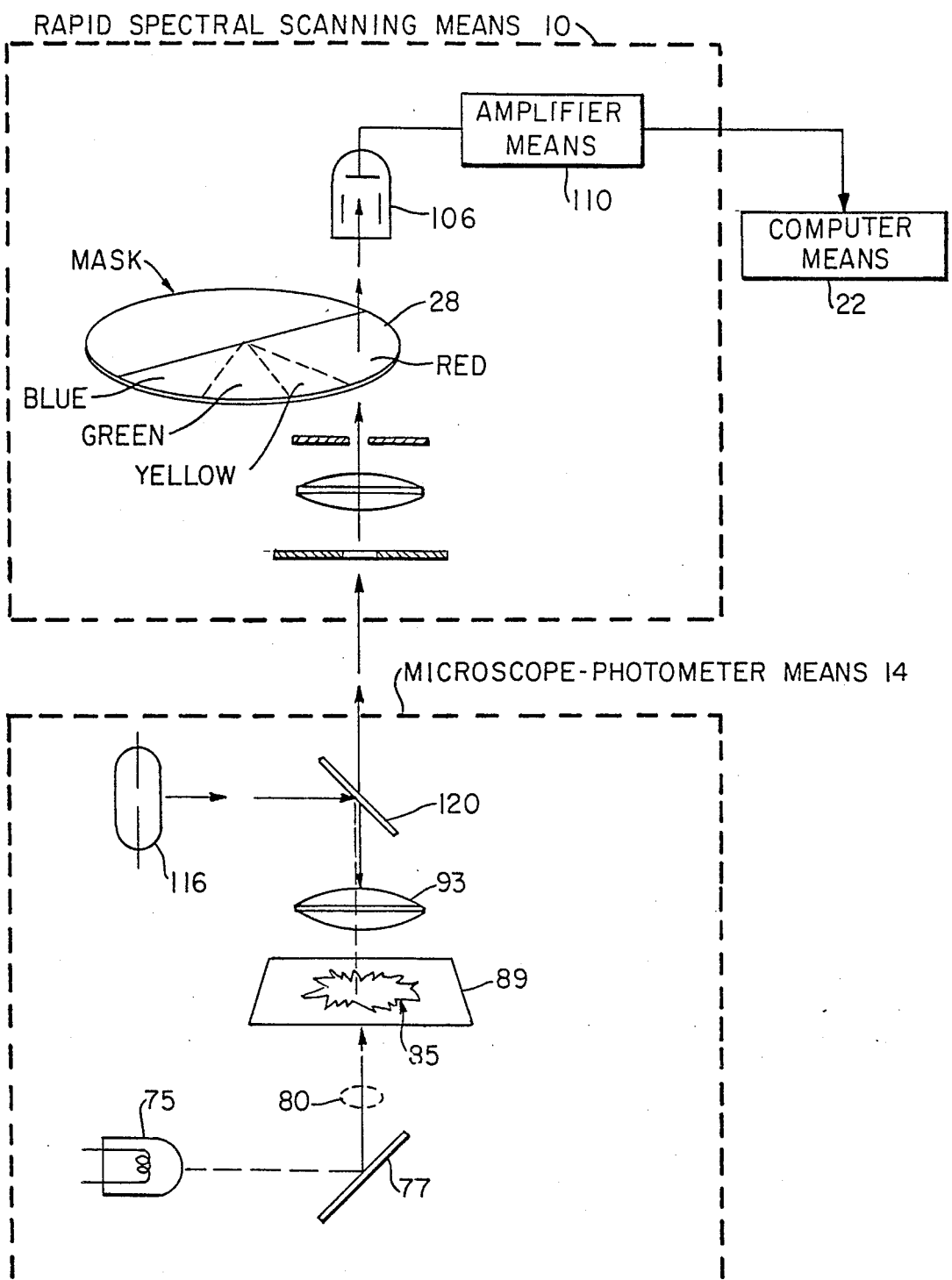
FIG. 5 is a simplified schematic of light flow and conversion to an electrical signal in the system shown in FIG. 1.

A schematic arrangement of the present invention is shown in FIG. 5. Microscope photometer means 14 includes a tungsten lamp source 75 which provides a beam of light that is reflected by a mirror 77 through a pinhole diaphragm 80. The beam of light passes through a rock sample 85 in a specimen plate 89. The light continues through an objective lens 93 and leaves the microscope photometer means 14 to enter rapid spectral scanning means 10 where it passes through a diaphragm 93, and through slit 69 of slit plate 66 in cover plate 64. The narrow beam of light passes through filter disk 28, which as noted previously is revolving, where it impinges upon a photomultiplier 106. Photomultiplier 106 provides an electrical output relating to the intensity of the light striking it. The signal from photomultiplier 106 is amplified by amplifier means 110. The amplified signal is provided to computer means 22.

Microscope-photometer means 14 also includes an ultraviolet lamp 116 which provides a beam of light to a beam splitter 120. The light is reflected down to rock sample 85 and causes rock sample 85 to provide fluorescence light with the fluorescence light being provided to the rapid spectral scanning means 10 as hereinbefore discussed for the transmitted light that has passed through rock sample 85. Thus, the light provided to filter disk 28 includes either transmitted light from the tungsten lamp source or fluorescence light from the fluorescence of rock sample 85. These illumination systems are alternately used on the same rock sample material.

Figure 6:
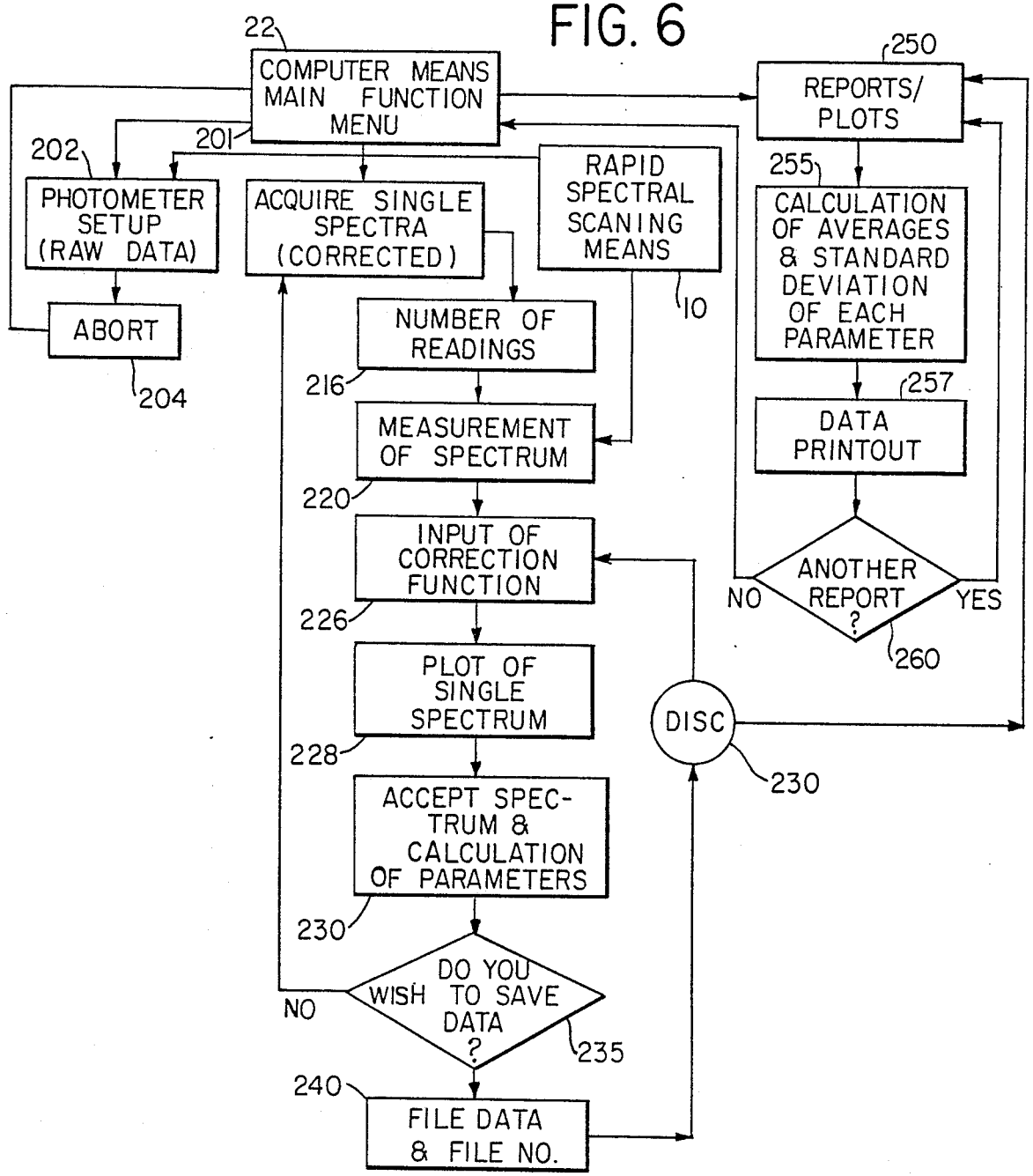
FIG. 6 is a simplified flow diagram of a program for practicing the present invention utilizing the computer means shown in FIGS. 1 and 5.

With reference to FIG. 6 there is shown a simplified block diagram of the functioning of the present invention in which computer means 22 main function menu (block 201), that is its basic program, is utilized to provide a signal to the microscope photometer means 14 for a raw data setup (block 202) and from there proceeds to an abort decision listed in block 204 to determine whether there is sufficient light or if the light is too overpowering for running the analysis.

Once it is determined that the microscope photometer means 14 is in operable condition for the analysis, the main function menu in block 201 then goes to the next step in which a single spectrum is acquired (block 210). This involves determining the number of readings to be taken as per block 216, which is performed in the "Measurement of the Spectrum", block 220. Block 220 represents receiving the signals from the rapid spectral scanning means 10.

The next step is the correcting of the spectrum as provided for in the "Input of Correction Function", block 226, and receiving correction data from a disk 230. The corrected data is then provided in the form of a plot by the step entitled "Plot of Signal Spectrum" 228. Block 230 provides for the acceptance of the spectrum and calculations of parameters which will be explained more fully hereinafter. The next subsequent step is a decision step to determine whether to save the data or not. A "no" decision proceeds back to "acquire single spectra data" block 210 again. If the decision is to save the data, the data is provided to "File Data and File Number", block 240, which in turn, after the proper encoding, provides it to disk 230.

Computer means 22 through its main function menu block 201 provides conventional type outputs for reports and plots as shown in block 250. Further, the information can be provided for the calculations of averages and standard deviations of each parameter as provided for in block 255, which results in a data printout as shown by block 257. Another decision block 260 has the determination of whether another report is desired. If the answer is yes, the operator is returned to the reports and plots block 250. If the answer is no, the operator is returned back to the main function menu, block 201.

Figure 7:
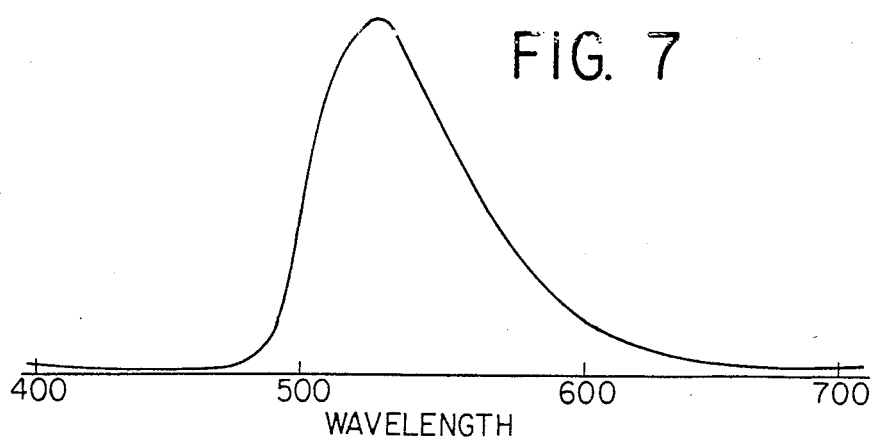
FIG. 7 shows a spectral analysis output provided by the system of the present invention.

FIG. 7 shows an acquired single spectra. The data associated with FIG. 7 and printed out with the spectra, includes: the peak wavelength, half intensity width is 531.7 nm, lower half intensity wavelength is 502.5 nm, the upper half intensity wavelength is 565.9 nm, half intensity width is 63.3 nm, the yellow-red part of half width value is −4.1 nm, the ratio of profile areas is 0.6808 and trichromatic coefficients X and Y are 0.2873 and 0.6313, respectively. It should be noted that the negative value for the yellow-red parameter occurs when the line for the yellow-red parameter falls short of a fixed reference wavelength which is 570 nm. The negative value is the distance in wavelength that the yellow-red parameter falls short. When the yellow-red parameter line exceeds the 570 nm reference, the excess is shown as a positive value for the yellow-red parameter. All of the parameters just referred to are well known in the art.

The present invention as hereinbefore described is an optical spectral analysis system with rapid spectral scanning. Although a rotational speed of 60 revolutions per second has been disclosed, the rotational speed may be increased. The limiting factor would be the ability of the system to provide good spectral resolution.

What is claimed is:

1. An optical spectral analyzer comprising:
   means for holding a specimen;
   means for transmitting light through a held specimen;
   means for causing the specimen to provide fluorescence light;
   filter means for filtering the light from the specimen in a predetermined manner, said means includes:
   filter disk means for being rotated through the light from the specimen so as to filter the light through a range of light wavelengths between 400 nm and 700 nm at least once per revolution, and
   rotator means for rotating the filter disk means;
   signal means receiving the filtered light for providing an intensity signal representative of the intensity of the filtered light; and
   output means connected to the signal means for providing a spectral output in accordance with the intensity signal from the signal means.

2. A system as described in claim 1 wherein the signal means includes:
   a photomultiplier tube receiving the filtered light, and
   means connected to the photomultiplier tube and the output means for amplifying the signal from the photomultiplier tube to provide the intensity signal to the output means.

3. A system as described in claim 1 wherein the rotator means rotates the disk means in a manner so that the filter intercepts the light from the specimen in a continuous manner through the predetermined range of wavelengths.

4. A system as described in claim 3 wherein the filter disk has a filter on one half of the disk and a mask filter on the other half of the disk.

5. An optical spectral analysis method comprising the steps of:
   transmitting light through specimen during a predetermined time period,
   causing the specimen to provide fluorescence light during another predetermined time period,
   rotating a filter disk through the light from the specimen so as to filter the light through a range of light wavelengths between 400 nm and 700 nm at least once per revolution, providing an intensity signal representative of the intensity of the filtered light, and providing a spectral output in accordance with the intensity signal.

6. A method as described in claim 5 in which the filtering step includes:

mounting two substantially identical filters in such a way that the light from the specimen is filtered through the predetermined range of wavelengths twice per revolution of the filter disk.

7. A method as described in claim 6 wherein the rotating step includes:

rotating the filter disk in a manner so that the light from the specimen is filtered in a continuous manner through the predetermined range of wavelengths.

8. A method as described in claim 7 wherein the intensity signal step includes:

using a photomultiplier tube to receive and convert the received filtered light to a signal, and amplifying the signal from the photomultiplier tube to provide the intensity signal to the output means.

* * * * *